United States Patent
Stout et al.

(10) Patent No.: US 12,419,553 B2
(45) Date of Patent: Sep. 23, 2025

(54) CAPILLARY TUBE CLOSURE

(71) Applicant: ACCU-GLASS LLC, St. Louis, MO (US)

(72) Inventors: Craig Stout, Port Matilda, PA (US); Thomas Pesch, St. Louis, MO (US); William Blakeney Harrison, St. Louis, MO (US); Paul Anthony Vitale, St. Louis, MO (US)

(73) Assignee: ACCU-GLASS LLC, St. Louis, MO (US)

( * ) Notice: Subject to any disclaimer, the term of this patent is extended or adjusted under 35 U.S.C. 154(b) by 819 days.

(21) Appl. No.: 17/650,000

(22) Filed: Feb. 4, 2022

(65) Prior Publication Data

US 2023/0248280 A1 Aug. 10, 2023

(51) Int. Cl.
*A61B 5/15* (2006.01)
*B01L 3/00* (2006.01)

(52) U.S. Cl.
CPC .. *A61B 5/150351* (2013.01); *A61B 5/150022* (2013.01); *B01L 3/50825* (2013.01)

(58) Field of Classification Search
None
See application file for complete search history.

(56) References Cited

U.S. PATENT DOCUMENTS 4,133,304 A * 1/1979 Bailey ............... A61B 5/150511
600/577
5,065,768 A 11/1991 Coleman et al.

* cited by examiner

Primary Examiner — Jay B Shah
(74) Attorney, Agent, or Firm — Vedder Price P.C.

(57) ABSTRACT

A closure adapted for insertion in a tube having a first end and an opposed second end and a bore extending therethrough. The tube adapted to draw a liquid into the tube by virtue of capillary action. The closure at least partially insertable in the first end and adapted to be slidably movable between a first position and a third position. The closure includes a substantially cylindrical body having an outer surface and a proximal end adapted to be inserted inside the bore and a distal end in close proximity with the first end. The body having a plurality of channels extending along the outer surface between the proximal end and the distal end, and a seal region extending along a periphery of the outer surface between the distal end and the plurality of channels.

20 Claims, 2 Drawing Sheets

CAPILLARY TUBE CLOSURE

TECHNICAL FIELD

The present invention is directed to closures, and more particularly, to closures adapted for insertion in tubes, such as tubes adapted to draw a liquid into the tube by virtue of capillary action or a fluid by gravitational action.

BACKGROUND

Capillary tubes are often used to collect blood samples for diagnostic and other testing purposes. These capillary tubes can be made of glass or plastic and are often sealed on one end after filling to enable further processing without leakage. The following problems can occur during filling, sealing, and processing:
- slow fill when some pre-inserted closures have limited venting;
- tube will not fill when some pre-inserted clay closures are not vented adequately;
- tube will not fill when some pre-inserted closures are prematurely sealed (e.g., the pre-inserted closures would fail if it was accidentally pressed in prior to filling);
- tube breakage when the tubes are closed, such as when pressing into clay; and/or
- tube breakage or leakage during centrifugation, causing loss of sample and equipment contamination.

It is commonly understood that a major source of biohazardous exposure when using capillary tubes in a laboratory process occurs due to capillary tube leakage after filling and during processing with multiple causes of tube leakage listed below, including:
- poor insertion of clay closures;
- poor seal of pre-inserted clay-based closures;
- inadequate time allowed from sealing to processing as some closures require at least 30 seconds to adequately seal;
- closures require the tube to be vertical to be properly inserted;
- a full tube leaves no remaining volume for the closure to be inserted, and inserting the closure in a full tube can push the liquid sample out either end of the tube; and/or
- over pressure of the tube into the sealing compound.

There is a need for closures adapted for insertion in capillary tubes that do not suffer from these drawbacks.

SUMMARY

In one example embodiment, a tube assembly includes a tube having a first end and an opposed second end and a bore extending therethrough, the tube adapted to draw a liquid into the tube by virtue of capillary action or a fluid by gravitational action. The tube assembly further includes a closure at least partially inserted in the first end and adapted to be slidably movable between a first position and a third position. The tube assembly further includes the closure including a substantially cylindrical body having an outer surface and a proximal end inserted inside the bore and a distal end in close proximity with the first end, the body having a plurality of channels extending along the outer surface between the proximal end and the distal end, and a seal region extending along a periphery of the outer surface between the distal end and the plurality of channels. With the closure in the first position, vapor contained in the bore is adapted to exit the bore from the first end via a plurality of passageways each defined by the bore and a corresponding channel in response to the liquid being drawn into the tube bore by capillary action. With the closure in a second position, the seal region is sufficiently inserted inside of the first end, defining a fluid tight seal therebetween and preventing the drawn liquid within the tube bore from escaping. In response to slidable movement of the closure relative to the tube from the second position toward the third position, at least a portion of the liquid inside the bore is urged to exit the tube from the second end.

In another example embodiment, a closure adapted for insertion in a tube having a first end and an opposed second end and a bore extending therethrough, the tube adapted to draw a liquid into the tube by virtue of capillary action, the closure at least partially insertable in the first end and adapted to be slidably movable between a first position and a third position, the closure includes a substantially cylindrical body having an outer surface and a proximal end adapted to be inserted inside the bore and a distal end in close proximity with the first end, the body having a plurality of channels extending along the outer surface between the proximal end and the distal end, and a seal region extending along a periphery of the outer surface between the distal end and the plurality of channels. With the closure in the first position, vapor contained in the bore is adapted to exit the bore from the first end via a plurality of passageways each defined by the bore and a corresponding channel in response to the liquid being drawn into the tube by capillary action. With the closure in a second position, the seal region is sufficiently inserted inside of the first end, defining a fluid tight seal therebetween and preventing the drawn liquid within the tube bore from escaping. In response to slidable movement of the closure relative to the tube from the second position toward the third position, at least a portion of the liquid inside the bore is urged to exit the tube from the second end.

In yet another example embodiment, a capillary tube assembly includes a tube having a first end and an opposed second end and a bore extending therethrough, the tube adapted to draw a liquid into the tube by virtue of capillary action, and a closure at least partially inserted in the first end and adapted to be slidably movable between a first position and a third position. The capillary tube assembly further includes the closure including a substantially cylindrical body having an outer surface and a proximal end inserted inside the bore and a distal end in close proximity with the first end, the body having a plurality of channels extending along the outer surface between the proximal end and the distal end, and a seal region extending along a periphery of the outer surface between the distal end and the plurality of channels. With the closure in the first position, vapor contained in the bore is adapted to exit the bore from the first end via a plurality of passageways each defined by the bore and a corresponding channel in response to the liquid being drawn into the tube bore by capillary action. With the closure in a second position, the seal region is sufficiently inserted inside of the first end, defining a fluid tight seal therebetween and preventing the drawn liquid within the tube bore from escaping. In response to slidable movement of the closure relative to the tube from the second position toward the third position, at least a portion of the liquid inside the bore is urged to exit the tube from the second end.

Other features and advantages of the present invention will be apparent from the following more detailed description, taken in conjunction with the accompanying drawings which illustrate, by way of example, the principles of the invention.

BRIEF DESCRIPTION OF THE DRAWINGS

Wherever possible, the same reference numbers will be used throughout the drawings to represent the same parts.

DETAILED DESCRIPTION OF EXAMPLE EMBODIMENTS

Figure 1:
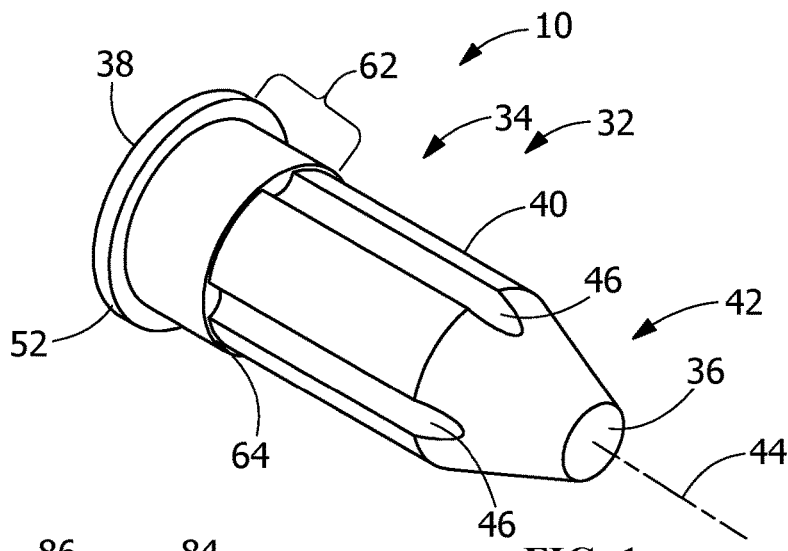
FIG. 1 is an upper perspective view of an exemplary closure.
Figure 6:
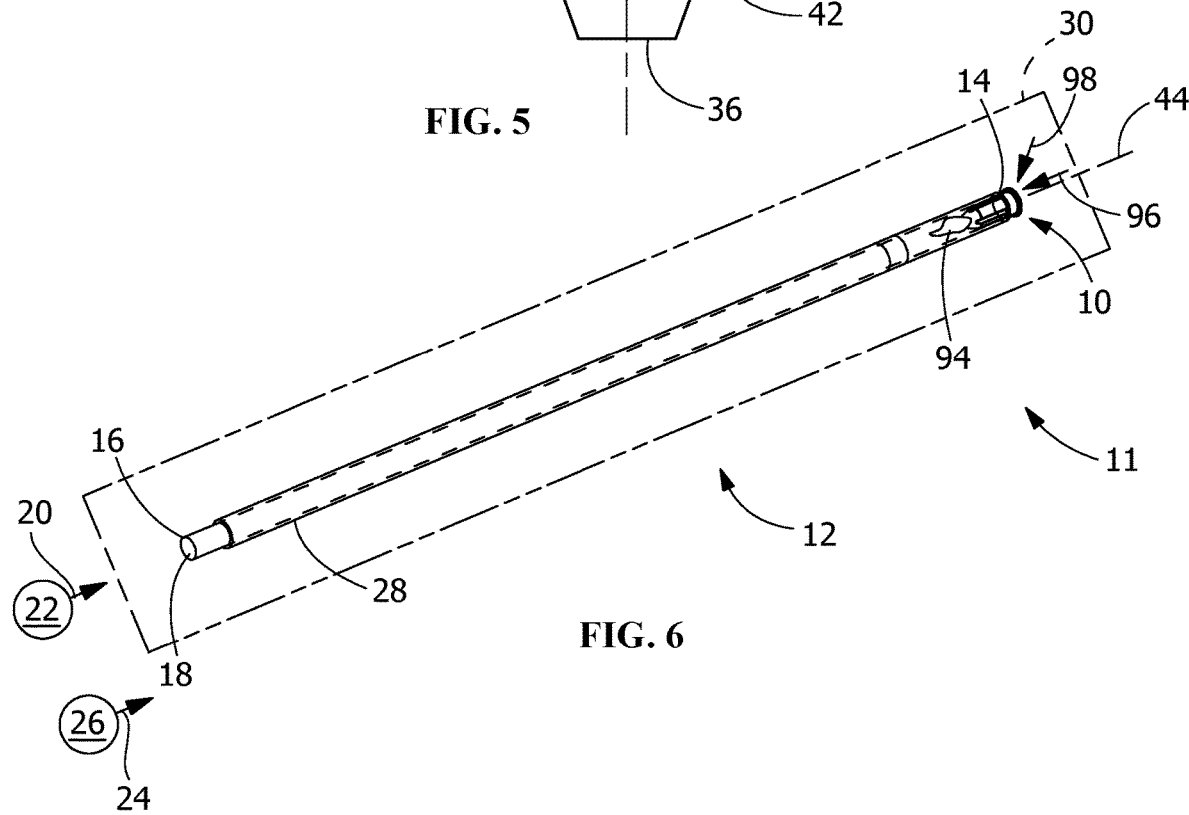
FIG. 6 is an upper perspective view of an exemplary capillary tube assembly.

FIG. 1 shows a closure 10 that is adapted to be insertable or received in a tube 12 (FIG. 6) such as a capillary tube. In one embodiment, capillary tube 10 is suitable for use with blood as the liquid, typically referred to as a hematocrit tube. More specifically, as shown in FIG. 6 for a tube assembly 11 such as a capillary tube assembly, tube 12 includes a first end 14, a second end 16, and a bore 18 extending therethrough, thereby connecting the ends 14, 16 in fluid communication therebetween. In one embodiment, tube 12 is adapted to draw a liquid 20 such as from a liquid source 22 into bore 18 through second end 16 by virtue of capillary action with closure 10 at least partially inserted in first end 14. Alternately, tube 12 is adapted to draw or receive a fluid 24 such as from a fluid source 26 into bore 18 through second end 16 by virtue of gravitational action with closure 10 at least partially inserted in first end 14. If tube 12 is uniform in size/shape at ends 14, 16, it is to be understood that ends 14, 16 could be exchanged or swapped or otherwise reversed end for end, and the arrangement with closure 10 being inserted in the opposite tube end (i.e., second end 16) would also operate as intended, except tube 12 would be adapted to draw liquid 20 from liquid source 22 into bore 18 through first end 14 by virtue of capillary action with closure 10 at least partially inserted in second end 16. Once bore 18 of tube 12 is sufficiently filled with liquid 20, and the novel closure 10 is slidably moved relative to tube 12 to secure the liquid therein as will be discussed in further detail below, tube 12 may then be placed in a centrifuge 30 to begin testing the liquid.

Optionally, as shown in FIG. 6, a protective layer 28 such as a transparent or translucent layer overlies an outer surface of tube 12, permitting an operator or user to view the contents (e.g., liquid 20 or fluid 24) in bore 18 of tube 12.

It is to be understood that the positions of ends 14, 16 of tube 12 relative to one another does not matter if tube 12 is a capillary tube receiving liquid 20, since capillary action can overcome gravity. However, in order for tube 12 to draw or receive a non-liquid fluid (e.g., a powder or granulated material) into bore 18 through an open end by gravitational action, the open end receiving the non-liquid fluid must be positioned at least partially vertically above the opposed end in which closure 10 is at least partially inserted.

Returning now to FIG. 1, closure 10 includes a substantially cylindrical body 32 having an outer surface 34 extending between a proximal end 36 adapted for insertion in first end 14 (FIG. 6) of tube 12 (FIG. 6) and inside of bore 18, and an opposed distal end 38 that is in close proximity with first end 14 upon insertion of proximal end 36 of closure 10 in first end 14 (FIG. 6) of tube 12 (FIG. 6). As shown, body 32 extends along an axis 44. Preferably, axis 44 is a central axis or axis of symmetry. In one embodiment, body 32 is substantially ovular. In one embodiment, body 32 is substantially circular. In other embodiments, body 32 may define other shapes. Body 32 includes a shank portion 40 extending to a narrowing tapered portion 42 that is positioned between shank portion 40 and proximal end 36. As shown, tapered portion 42 defines a frustum of a right cone or continuous peripheral chamfer formed in the peripheral edge of proximal end 36. Optionally, tapered portion 42 defines a curved peripheral edge (FIG. 4) formed in the peripheral edge of proximal end 36. Optionally, tapered portion 42 may define an oblique ovular cone (i.e., having an axis that is not coincident with axis 44), which includes an oblique circular cone, so long as the distal end does not interfere with insertion of the distal end in a tube.

Figure 4:
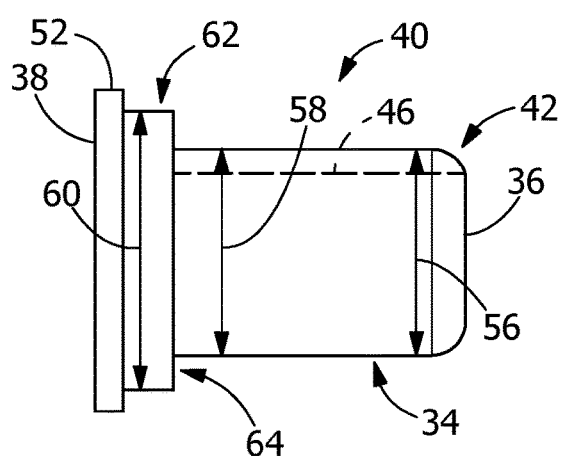
FIG. 4 is an elevation view of an exemplary closure.

In one embodiment, as shown in FIG. 4, shank portion 40 has a diameter 56 that is proximate to tapered portion 42, which diameter 56 being equal to a diameter 58 of shank portion 40 that is proximate to distal end 38. Both diameters 56, 58 of shank portion 40 are less that a diameter 60 of a sealing portion 60. In one embodiment, diameter 56 may be slightly greater than diameter 58. In one embodiment, diameter 56 may be slightly less than diameter 58. That is, the magnitudes of diameters 56, 58 of different positions of shank portion 40 may be different from one another, so long as outer surface 34 of shank portion 40 of the closure permits sliding frictional movement of tube 12 (FIG. 6) relative to the closure between different positions, as will be discussed in further detail below.

Figure 3:
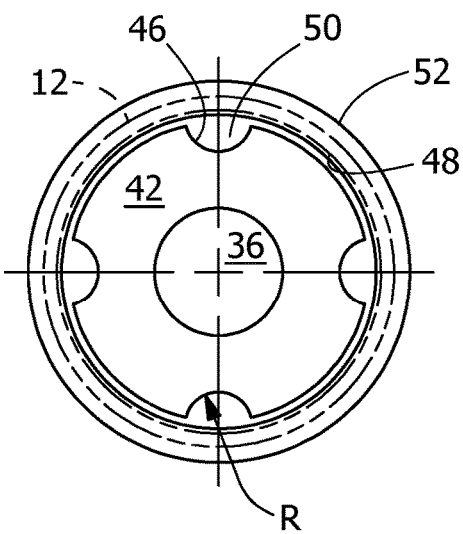
FIG. 3 is an end view of the closure of FIG. 1 at least partially inserted in an exemplary tube.

As further shown in FIG. 1, opposite proximal end 36 of body 32 of closure 10 is distal end 38, which distal end 38 includes an outwardly extending flange 52. A shoulder 64 separates shank portion 40 from a seal region 62 that extends along a periphery of outer surface 34 between distal end 38 and channels 46. That is, seal region 62 has a larger cross-sectional area than shank portion 40, and is without channels. However, the cross-sectional area of seal region 62 is equal to or slightly greater than the cross sectional area defining the inner wall of tube 12 (FIG. 6) as measured by the intersection with a plane (not shown) that is perpendicular to axis 44. As a result, in response to sufficient insertion of body 32 inside of tube 12 (FIG. 6) such that first end 14 (FIG. 6) of tube 12 (FIG. 6) is directed over proximal end 36 of body 32 until first end 14 (FIG. 6) extends past shoulder 64, placing a portion of the inner wall 48 (FIG. 3) of the tube in contact with seal region 62, a fluid tight seal is established between the circumferential surface of seal region 62 and first end 14 of the tube, preventing a flow of any of air, liquid or fluid therethrough.

Figure 2:
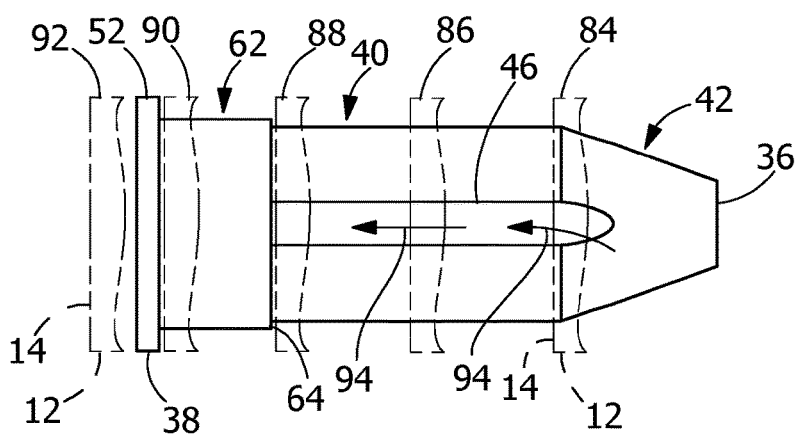
FIG. 2 is an elevation view of the closure of FIG. 1 showing different insertion positions of the closure relative to an exemplary tube.

In one embodiment, such as at or in close proximity of the base of flange 52, perforations may be formed, permitting flange 52 to be sheared away or otherwise separated from body 32, permitting body 32 to be inserted inside of tube 12 (FIG. 6) (e.g., closure insertion position 92 (FIG. 2).

As further shown in FIG. 1, body 32 has a plurality of channels 46, such as four (FIG. 3) extending along outer surface 34 between proximal end 36 and distal end 38 substantially parallel to axis 44, and more specifically, being formed in shank portion 40 and at least a portion of tapered portion 42. In response to proximal end 36 of closure 10 being at least partially inserted in tube 12, i.e., sufficiently inserted such that an inner wall surface 48 (FIG. 3) of tube 12 (FIG. 3) has been slid over proximal end 36 and partially surrounds shank portion 40, the corresponding inner wall surfaces 48 (FIG. 3) of the tube and channels 46 of the closure each define passageways 50 (FIG. 3) for permitting a flow of air displaced from the tube as the tube is drawing liquid 20 (FIG. 6) or fluid 22 (FIG. 6) therein. As shown, channels 46 may each define a substantially circular profile having a radius R (FIG. 3) formed in shank portion 44 and tapered portion 42 that have or define a uniform cross section. Stated another way, shank portion 40 has a substantially uniform cross section along its length defined by cross sections taken perpendicular to axis 44. In one embodiment, at least a portion of at least one channel 46 has or defines a nonuniform cross section. In one embodiment, the number of channels 46 may be different than four, and which channels may be arranged symmetrically or non-symmetrically about axis 44. In one embodiment, at least a portion of one channel 46 may be sized or shaped differently than at least a portion of one or more other channels.

Channels 46 may define any shape permitting by an injection molding process of a suitable closure material. Suitable closure materials include elastically compressible or resilient materials, such as an elastomer or other materials. For example, in one embodiment, the closure is composed of Santoprene™ owned by ExxonMobil. In one embodiment, an outer surface of the closure has a coefficient of friction less than 0.5. In one embodiment, an outer surface of the closure has a coefficient of friction less than 0.25. In one embodiment, the closure has a pigment that visually contrasts with the fluid or liquid to be inserted into the tube. In one embodiment, the closure has a pigment that visually contrasts with blood.

Preferably, body 32 of closure 10 is symmetrical about axis 44 including the radial arrangement of channels 46 formed therein.

Figure 5:
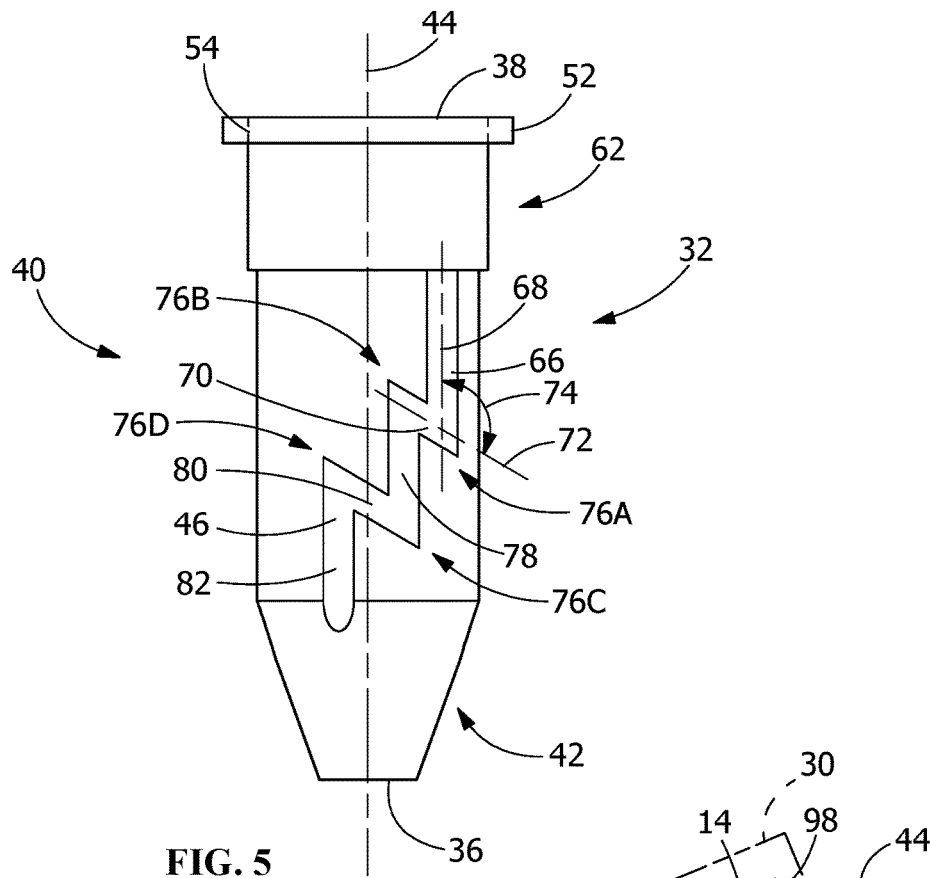
FIG. 5 is an elevation view of an exemplary closure.

Referring now to FIG. 5, at least a portion of at least one channel 46 (FIG. 5 only shows one channel) has or defines a tortuous path, involving at least one flow direction change. For example, as shown in FIG. 5, channel 46 includes interconnected channel portions 66, 70, 78, 80, 82. In one embodiment, one of more the channels may have a number of channel portions different than five. As further shown, channel portion 66 has an axis 66 that is substantially parallel to axis 44 of body 32. Channel portion 70 having an axis 72 interconnects with and extends from channel portion 66, subtending an obtuse angle between axes 66, 72 therebetween and defining a flow direction change 76A (i.e., channel portion 66 proceeds along axis 66 away from seal region 62 toward tapered portion 42, and upon channel portion 66 extending or transitioning to channel portion 72 at flow direction change 76A, channel portion 72 proceeds along axis 72 away from tapered portion 42). As further shown in FIG. 5, channel portions 78, 82 each have a respective axis (not shown) that is parallel to axis 66, and channel portion 80, which is interconnected at opposed ends between channel portions 78, 82, has an axis (not shown) that is parallel to axis 72. In other words, a liquid or fluid flowing along channel 46 from seal region 62 to tapered portion 42 via interconnected channel portions 66, 70, 78, 80, 82 undergoes four respective abrupt directional changes 76A, 76B, 76C, 76D each defining an obtuse angle between each of the corresponding five respective channel portions. In one embodiment, at least one of the interconnected channel portions may define an acute angle between their corresponding axes. In one embodiment, none of the channel portions may be parallel to the closure axis. In one embodiment, one or more of the channel portions may be parallel to the closure axis. In one embodiment, at least one channel portion may be sized differently than or define a different profile compared to at least one other channel portion, whether directly interconnected (i.e., immediately adjacent or directly extending from one channel portion to another channel portion), or not directly interconnected. In one embodiment at least a portion of at least one channel portion may be curved (versus being substantially straight) and contain or otherwise incorporate a change of direction along its respective length or extent having an angular magnitude anywhere between one degree and 180 degrees, or more than 180 degrees (e.g., an unclosed or uncrossed curve such as defined by an arc or perimeter of an ovular or circular segment having an angle of greater than 180 degrees, but less than 360 degrees). In one embodiment, any one of the one or more channels may have differently arranged flow patterns (i.e., any combination of different arrangements of channel portions).

FIG. 2 shows several different insertion positions 84, 86, 88, 90, 92 of closure 10 (FIG. 6) relative to end 14 of tube 12 as a result of slidable movement of the closure relative to the end of the tube. More specifically, the closure insertion positions inside of end 14 of tube 12 filled with vapor 94 such as air (i.e., an initially empty tube, or empty bore 18 (FIG. 6)), and the effect the closure insertion positions have on the flow of vapor 94 via passageways 50 (FIG. 3) to exit bore 18 (FIG. 6) from end 14 in response to, for example, liquid 20 (FIG. 6) being drawn from liquid source 22 (FIG. 6) into bore 18 (FIG. 6) through end 16 (FIG. 6) such as by capillary action, are now discussed. In other words, as liquid 20 (FIG. 6) is drawn into bore 18 (FIG. 6) from end 16 (FIG. 6), vapor 94 (FIG. 6) initially contained in the bore of the tube is displaced and exits the tube from end 14 (FIG. 6), as permitted by virtue of the extent of the different closure insertion positions.

That is, as further shown in FIG. 2, with the closure in closure insertion position 84 at the juncture of shank portion 40 and tapered portion 42, vapor 94 contained in bore 18 (FIG. 6) of the tube is adapted to exit the bore from end 14 via passageways 50 (FIG. 3) each defined by the bore and a corresponding channel 46 (FIG. 3) in response to liquid 20 (FIG. 6) being drawn into the tube bore by capillary action.

As further shown in FIG. 2, with the closure being slidably inserted further inside of end 14 of the tube from closure insertion position 84 to closure insertion position 86 positioned over and surrounding a portion of shank portion 40, vapor 94 contained in bore 18 (FIG. 6) is still capable of exiting bore 18 (FIG. 6) from end 14 via the passageways 50 (FIG. 3) in response to liquid 20 (FIG. 6) being drawn into the tube bore by capillary action.

As further shown in FIG. 2, with the closure being slidably inserted further inside of end 14 of the tube from closure insertion position 86 to closure insertion position 88 at the juncture of seal region 62 and shank portion 40, a fluid tight seal is established. More specifically, once the inner wall surface 48 (FIG. 3) of the tube makes sufficient contact with the peripheral edge of shoulder 64 (FIG. 4) of the closure, and more preferably, the closure is even further inserted inside of end 14 of the tube, such as toward, and/or including, closure insertion position 90 at the juncture of the base of flange 52 of distal end 38 and seal region 62 of the closure (the fully inserted position of the closure inside of the tube, except for flange 52), not only is vapor 94 (FIG. 6) contained in bore 18 (FIG. 6) prevented from exiting bore 18 (FIG. 6) from end 14 via the passageways 50 (FIG. 3) in response to liquid 20 (FIG. 6) being drawn into the tube bore by capillary action, but liquid drawn into the bore via capillary action is also prevented from escaping from either of ends 14, 16 (FIG. 6), permitting the tube assembly to be directly placed in a centrifuge 30 (FIG. 6) with the closure radially outwardly from the rotational axis (not shown) of the centrifuge, such that the fluid tight seal between the closure and the tube is further enhanced. In other words, with the closure positioned anywhere between closure insertion position 88 and closure insertion position 90, (and preferably at or in close proximity to closure insertion position 90), the liquid in the tube is prevented from escaping, and is commonly referred to as the liquid in the tube being "sealed".

As further shown in FIG. 2, with the closure at closure insertion position 90, such that the closure is fully inserted (except for flange 52), in response to yet further inserting the closure inside of end 14 of the tube from closure insertion position 90 toward closure insertion position 92, the entire closure is now fully inserted inside of the tube, as distal end 38 is slidably moved along axis 44 (FIG. 6) of the tube toward end 16 (FIG. 6). That is, for example, if the base of flange 52 in close proximity to the periphery defined by seal region includes perforations 54 (FIG. 5) formed therein, a toroidal portion of flange 52 is sheared away from distal end 38, permitting the closure to be further slidably inserted inside of end 14 of the tube, and in fact, permitting the entire closure to be slidably moved away from end 14 toward end 16 (FIG. 6) of the tube. In this arrangement, as a result of the sliding fluid tight seal between the tube and seal region 62, in response to continued insertion of the closure inside of end 14 of the tube toward end 16 (FIG. 6), liquid 20 (FIG. 6) previously drawn into the bore of the tube by capillary action could be urged to exit the tube from end 16 (FIG. 6). This advantageously provides the ability to selectively remove at least a portion of the liquid from the tube as desired (e.g., the closure acting as a plunger or piston, in effect).

In order to slidably move the closure inside of the tube between any of the closure insertion positions 84, 86, 88, 90, 92 as shown in FIG. 2, a force 96 (FIG. 6) is applied parallel to axis 44 (FIG. 6). As a result of at least one and/or a combination of the low coefficient of friction (both static and dynamic) of the outer surface of the closure and the inner surface of the tube, the geometry and clearance tolerances between the different portions of the closure and the inner surface of the tube, including the degree of compressibility of the closure when inserted inside of the tube, the magnitude of force 96 required to slidably move the closure along axis 44 (FIG. 6) relative to the tube between closure insertion position 84 toward closure position 88, between closure insertion position 84 toward closure position 90, and between closure insertion position 84 toward closure position 92 is minimized, and is less than a predetermined force, while operating as intended, as previously discussed above. In one embodiment, force 96 is less than a predetermined force applied along axis 44 (FIG. 6) having a magnitude that could result in permanently damaging the tube. In one embodiment. In one embodiment, force 98 (which is force 96 applied at a nonzero angle relative to axis 44 (FIG. 6) is less than a predetermined force applied parallel to force 98 (FIG. 6) having a magnitude that could result in permanently damaging the tube. In other words, in these embodiments, the installation force required to slidably move the closure between the desired closure insertion positions is insufficient to permanently damage the tube, irrespective of which direction and the location at which the installation force is applied to the tube.

It is to be understood that the various descriptions of the embodiments disclosed herein have been simplified to illustrate only those elements, features, and aspects that are relevant to a clear understanding of the disclosed embodiments, while eliminating, for purposes of clarity, other elements, features, and aspects. Persons having ordinary skill in the art, upon considering the present description of the disclosed embodiments, will recognize that other elements and/or features may be desirable in a particular implementation or application of the disclosed embodiments. However, because such other elements and/or features may be readily ascertained and implemented by persons having ordinary skill in the art upon considering the present description of the disclosed embodiments, and are therefore not necessary for a complete understanding of the disclosed embodiments, a description of such elements and/or features is not provided herein. As such, it is to be understood that the description set forth herein is merely exemplary and illustrative of the disclosed embodiments and is not intended to limit the scope of the invention as defined solely by the claims.

In the present disclosure, other than where otherwise indicated, all numbers expressing quantities or characteristics are to be understood as being prefaced and modified in all instances by the term "about." Accordingly, unless indicated to the contrary, any numerical parameters set forth in the following description may vary depending on the desired properties one seeks to obtain in the embodiments according to the present disclosure. At the very least, and not as an attempt to limit the application of the doctrine of equivalents to the scope of the claims, each numerical parameter described in the present description should at least be construed in light of the number of reported significant digits and by applying ordinary rounding techniques.

Also, any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10. Any maximum numerical limitation recited herein is intended to include all lower numerical limitations subsumed therein and any minimum numerical limitation recited herein is intended to include all higher numerical limitations subsumed therein. Accordingly, Applicant reserves the right to amend the present disclosure, including the claims, to expressly recite any sub-range subsumed within the ranges expressly recited herein. All such ranges are intended to be inherently disclosed herein such that amending to expressly recite any such sub-ranges would comply with the requirements of 35 U.S.C. § 112, first paragraph, and 35 U.S.C. § 132(a).

The grammatical articles "one", "a", "an", and "the", as used herein, are intended to include "at least one" or "one or more", unless otherwise indicated. Thus, the articles are used herein to refer to one or more than one (i.e., to at least one) of the grammatical objects of the article. By way of example, "a component" means one or more components, and thus, possibly, more than one component is contemplated and may be employed or used in an implementation of the described embodiments.

Any patent, publication, or other disclosure material, in whole or in part, that is said to be incorporated by reference herein, is incorporated herein in its entirety, but only to the extent that the incorporated material does not conflict with existing definitions, statements, or other disclosure material expressly set forth in this disclosure. As such, and to the extent necessary, the express disclosure as set forth herein supersedes any conflicting material incorporated herein by reference. Any material, or portion thereof, that is said to be incorporated by reference herein, but which conflicts with existing definitions, statements, or other disclosure material set forth herein is only incorporated to the extent that no conflict arises between that incorporated material and the existing disclosure material.

While the invention has been described with reference to one or more embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. In addition, all numerical values identified in the detailed description shall be interpreted as though the precise and approximate values are both expressly identified.

What is claimed is:

1. A tube assembly comprising:
a tube having a first end and an opposed second end and a bore extending therethrough, the tube adapted to draw a liquid into the tube by virtue of capillary action or a fluid by gravitational action;
a closure at least partially inserted in the first end and adapted to be slidably movable between a first position and a third position;
the closure including:
a substantially cylindrical body having an outer surface and a proximal end inserted inside the bore and a distal end in close proximity with the first end, the body having a plurality of channels extending along the outer surface between the proximal end and the distal end; and
a seal region extending along a periphery of the outer surface between the distal end and the plurality of channels,
wherein with the closure in the first position, vapor contained in the bore is adapted to exit the bore from the first end via a plurality of passageways each defined by the bore and a corresponding channel in response to the liquid being drawn into the tube bore by capillary action,
wherein with the closure in a second position, the seal region is sufficiently inserted inside of the first end, defining a fluid tight seal therebetween and preventing the drawn liquid within the tube bore from escaping, and
wherein in response to slidable movement of the closure relative to the tube from the second position toward the third position, at least a portion of the liquid inside the bore is urged to exit the tube from the second end.

2. The tube assembly of claim 1, wherein each of the plurality of channels defines a tortuous path.

3. The tube assembly of claim 1, wherein at least a portion of at least one channel has a uniform cross section.

4. The tube assembly of claim 1, wherein at least a portion of at least one channel has a non-uniform cross section.

5. The tube assembly of claim 1, wherein the closure is composed of an elastically compressible material.

6. The tube assembly of claim 1, wherein a force sufficient to slidably move the closure from the first position toward the second position and from the second position toward the third position is less than a predetermined force.

7. The tube assembly of claim 6, wherein the predetermined force is a force applied along the longitudinal axis of the tube and having a magnitude insufficient to permanently damage the tube.

8. The tube assembly of claim 6, wherein the predetermined force is a force applied at a non-zero acute angle to the longitudinal axis of the tube and having a magnitude insufficient to permanently damage the tube.

9. The tube assembly of claim 1, wherein the closure is an elastomer.

10. The tube assembly of claim 1, wherein the capillary tube assembly is adapted to be placed in a centrifuge with the closure in the second position or the third position.

11. The tube assembly of claim 1, wherein the distal end includes a flange extending outwardly from the body, the flange is adapted to form a fluid tight seal in the third position.

12. The tube assembly of claim 11, wherein the flange is perforated.

13. The tube assembly of claim 11, wherein the flange is adapted to be separable from the distal end in response to a sufficient force applied to the distal end of the closure in the third position.

14. The tube assembly of claim 1, wherein the closure has a pigment visually contrasting with the fluid or the liquid.

15. The tube assembly of claim 1, wherein the closure has a pigment visually contrasting with blood.

16. The tube assembly of claim 1, wherein the proximal end is tapered.

17. The tube assembly of claim 1, wherein the outer surface has a coefficient of friction less than 0.5.

18. A closure adapted for insertion in a tube having a first end and an opposed second end and a bore extending therethrough, the tube adapted to draw a liquid into the tube by virtue of capillary action, the closure at least partially insertable in the first end and adapted to be slidably movable between a first position and a third position, the closure comprising:
a substantially cylindrical body having an outer surface and a proximal end adapted to be inserted inside the bore and a distal end in close proximity with the first end, the body having a plurality of channels extending along the outer surface between the proximal end and the distal end; and
a seal region extending along a periphery of the outer surface between the distal end and the plurality of channels,
wherein with the closure in the first position, vapor contained in the bore is adapted to exit the bore from the first end via a plurality of passageways each defined by the bore and a corresponding channel in response to the liquid being drawn into the tube by capillary action,
wherein with the closure in a second position, the seal region is sufficiently inserted inside of the first end, defining a fluid tight seal therebetween and preventing the drawn liquid within the tube bore from escaping, and
wherein in response to slidable movement of the closure relative to the tube from the second position toward the third position, at least a portion of the liquid inside the bore is urged to exit the tube from the second end.

19. The closure of claim 18, wherein the closure has a pigment visually contrasting with the fluid or the liquid.

20. A capillary tube assembly comprising:
a tube having a first end and an opposed second end and a bore extending therethrough, the tube adapted to draw a liquid into the tube by virtue of capillary action;

a closure at least partially inserted in the first end and adapted to be slidably movable between a first position and a third position;

the closure including:

a substantially cylindrical body having an outer surface and a proximal end inserted inside the bore and a distal end in close proximity with the first end, the body having a plurality of channels extending along the outer surface between the proximal end and the distal end; and a seal region extending along a periphery of the outer surface between the distal end and the plurality of channels, wherein with the closure in the first position, vapor contained in the bore is adapted to exit the bore from the first end via a plurality of passageways each defined by the bore and a corresponding channel in response to the liquid being drawn into the tube bore by capillary action, wherein with the closure in a second position, the seal region is sufficiently inserted inside of the first end, defining a fluid tight seal therebetween and preventing the drawn liquid within the tube bore from escaping, and wherein in response to slidable movement of the closure relative to the tube from the second position toward the third position, at least a portion of the liquid inside the bore is urged to exit the tube from the second end.

* * * * *